(12) United States Patent
Meinert et al.

(10) Patent No.: US 11,879,882 B2
(45) Date of Patent: Jan. 23, 2024

(54) SENSOR FOR DETERMINING A MEASURAND AND METHOD FOR DETERMINING A MEASURAND WITH A SENSOR

(71) Applicant: ENDRESS+HAUSER GROUP SERVICES AG, Reinach (CH)

(72) Inventors: Tobias Meinert, Freiburg (DE); Benjamin Scherer, Oberried (DE)

(73) Assignee: Endress+Hauser Group Services AG, Reinach (CH)

( * ) Notice: Subject to any disclaimer, the term of this patent is extended or adjusted under 35 U.S.C. 154(b) by 104 days.

(21) Appl. No.: 17/656,450

(22) Filed: Mar. 25, 2022

(65) Prior Publication Data
US 2022/0308030 A1    Sep. 29, 2022

(30) Foreign Application Priority Data
Mar. 25, 2021    (DE) .......................... 102021107594.7

(51) Int. Cl.
*G01N 33/00*    (2006.01)
*B01F 31/80*    (2022.01)

(52) U.S. Cl.
CPC .......... *G01N 33/0016* (2013.01); *B01F 31/80* (2022.01)

(58) Field of Classification Search
CPC .. G01N 33/0016; G01N 21/3504; G01N 1/38; B01F 31/80; B01F 31/86
See application file for complete search history.

(56) References Cited

U.S. PATENT DOCUMENTS

| 5,502,308 A * | 3/1996 | Wong .................... G08B 17/117 250/338.5 |
| 6,719,449 B1 * | 4/2004 | Laugharn, Jr. ...... B01F 35/2115 366/127 |
| 7,028,562 B2 * | 4/2006 | LaCourse .............. G01N 30/14 73/863.23 |

(Continued)

FOREIGN PATENT DOCUMENTS

| DE | 29701652 U1 | 4/1997 |
| DE | 10222165 A1 | 11/2003 |

(Continued)

*Primary Examiner* — Francis C Gray
(74) *Attorney, Agent, or Firm* — Christopher R. Powers; Endress+Hauser (USA) Holding, Inc.

(57) ABSTRACT

A sensor for determining a measurand dependent on a concentration of a gaseous analyte in a liquid medium includes: a closed measurement chamber with a gas sensor sensitive to the gaseous analyte for generating a measurement signal which is dependent on the concentration of the gaseous analyte in the measurement chamber; a diffusion membrane impermeable to liquid and gas-permeable to the gaseous analyte, which diffusion membrane closes the measurement chamber and includes a medium-contacting second surface; an evaluation unit for determining the measurand on the basis of the measurement signal; and an ultrasound emission unit designed to introduce ultrasonic waves into the medium such that a mixing of the medium is generated in a volume adjacent the medium-contacting second surface. Further disclosed is a method for determining the measurand dependent on the concentration of the gaseous analyte in the liquid medium using the disclosed sensor.

14 Claims, 2 Drawing Sheets

(56) References Cited

U.S. PATENT DOCUMENTS

2006/0260183 A1* 11/2006 Hockaday .............. A01M 1/02
43/132.1

FOREIGN PATENT DOCUMENTS

| DE | 102014203863 A1 | 9/2015 | |
|----|-----------------|--------|---|
| EP | 0871865 B1 * | 2/2003 | ......... G01N 21/8507 |
| FR | 3103892 A1 * | 6/2021 | ........... G01N 21/274 |
| WO | WO-2007043147 A1 * | 4/2007 | .......... B01F 11/0266 |

* cited by examiner

SENSOR FOR DETERMINING A MEASURAND AND METHOD FOR DETERMINING A MEASURAND WITH A SENSOR

The present application is related to and claims the priority benefit of German Patent Application No. 10 2021 107 594.7, filed on Mar. 25, 2021, the entire contents of which are incorporated herein by reference,

TECHNICAL FIELD

The present disclosure relates to sensors for determining a measurand dependent on a concentration of a gaseous analyte in a liquid medium, including a gas sensor sensitive to the gaseous analyte.

BACKGROUND

In a conventional gas sensor, the gaseous analyte diffuses from the liquid medium into a measurement chamber via a diffusion membrane that is impermeable to liquid and that is gas-permeable to the gaseous analyte. The diffusion membrane here closes off the measurement chamber. By means of the gas sensor, the measurand, which depends on the concentration of the gaseous analyte in the liquid medium, can then be determined on the basis of a measurement signal of the gas sensor, for example, by using electronic components configured for this purpose. During generation of the measurement signal in the measurement chamber, a pressure equilibrium between the measurement chamber and the liquid medium may preferably be present.

In the diffusion process, there is a diffusion rate which describes the diffusion of the gaseous analyte from the liquid medium into the measurement chamber. This diffusion rate determines the response time of the sensor. The response time of the sensor is defined, for example, as the time period after which a step response of the sensor taking place under a change in the concentration of the gaseous analyte in the liquid medium has followed the changed concentration to a large extent (e.g., 85%, 90%, 95%, etc.). For example, reference may be made at 90% to the "t90 time," which is determined under laboratory conditions and is generally known for the respective sensor and the respective gaseous analyte.

The diffusion rate is theoretically determined by the diffusion rate of the diffusion membrane which is specific to the respective gaseous analyte and is adjusted by the special design of the membrane (material properties, pore size, etc.). In practice, however, this represents only an upper limit. In the diffusion process, a depleted boundary layer, in which the concentration of the gaseous analyte is reduced, forms on the second, medium-contacting surface. In the depleted boundary layer, the proportion (or concentration) of the gaseous analyte is reduced; accordingly, less analyte can be delivered for diffusion through the diffusion membrane.

This applies, especially, but not exclusively, to the case of $CO_2$ as gaseous analyte. Further, during operation, the pores of the diffusion membrane can gradually clog up due to impurities. Both processes are a hindrance for the diffusion process and, therefore, lead in practice to a reduced effective diffusion rate and thus also to a correspondingly longer response time. A long response time is in principle disadvantageous and especially undesirable if the measurand is to be used as a control or a regulating variable, for example, in process and/or laboratory automation.

SUMMARY

The object of the present disclosure is, therefore, to improve the response time of such a sensor. The object is achieved by a sensor for determining a measurand dependent on a concentration of a gaseous analyte in a liquid medium and by a method for determining a measurand dependent on a concentration of a gaseous analyte in a liquid medium according to the present disclosure.

Regarding the sensor of the present disclosure, the object is achieved by a sensor for determining a measurand dependent on a concentration of a gaseous analyte in a liquid medium that comprises: a closed measurement chamber with a gas sensor sensitive to the gaseous analyte for generating a measurement signal which is dependent on the concentration of the gaseous analyte in the measurement chamber; a diffusion membrane which is impermeable to liquid and is gas-permeable to the gaseous analyte, which diffusion membrane closes off the measurement chamber with a first surface facing the measurement chamber and has a medium-contacting second surface; an evaluation unit for determining the measurand on the basis of the measurement signal of the gas sensor, and an ultrasound emission unit which is designed to introduce ultrasonic waves into the medium in such a way that mixing of the medium is generated in a volume adjacent to the medium-contacting second surface.

The ultrasonic waves initiate flow processes in the medium. These flow processes can comprise non-directed, for example, turbulent, and/or directed flows and cause mixing in the volume adjacent to the medium-contacting second surface. As a result of the mixing, fresh medium is transported to the medium-contacting second surface, or a removal of the depleted boundary layer is effected. Depending on the type of mixing and/or type of ultrasonic waves introduced, the diffusion membrane itself is also set in motion to a certain extent. In the case of a moving diffusion membrane, clogging of the pores is reduced and/or the pores are opened up again or even the diffusion of the gaseous analyte within the measurement chamber toward the gas sensor is also supported. All these processes therefore increase the effective diffusion rate and reduce the actual response time.

The ultrasonic waves serve here only for mixing the medium in the volume adjacent to the medium-contacting second surface and are explicitly not used in the context of the present disclosure to determine the concentration of the gaseous analyte in the medium by means of the ultrasound emission unit, for example, via a resonance frequency.

The ultrasound emission unit comprises, for example, at least one ultrasonic transducer for converting an excitation signal into ultrasonic waves as well as electronic components for generating the excitation signal. In addition to the ultrasound emission unit, no further means are preferably required for generating the mixing, such as operation of the sensor as a flow cell and/or another mechanical mixing by means of a stirrer.

In one embodiment of the present disclosure, the ultrasound emission unit is designed to emit ultrasonic waves at a frequency of at least 10 kHz, for example, at least 20 kHz.

In one embodiment of the present disclosure, the ultrasound emission unit comprises an emitting surface for emitting the ultrasonic waves that is arranged substantially in parallel to the diffusion membrane.

In an embodiment of the present disclosure, the ultrasound emission unit can be operated in a resonance mode, in which resonance mode a standing wave forms between the ultrasound emission unit and the diffusion membrane in the volume. The ultrasound emission unit is regulated for resonance, for example, by the evaluation unit of the sensor and/or the above-mentioned excitation unit. For example, an emitting surface of the ultrasound emission unit is arranged substantially in parallel to the diffusion membrane and the standing wave runs perpendicularly to the emitting surface and to the second surface of the diffusion membrane. In one embodiment of the last-mentioned embodiment, the ultrasound emission unit is therefore designed to generate in resonance mode a standing ultrasonic wave in the volume, which standing ultrasonic wave runs perpendicularly to the emitting surface and the diffusion membrane.

For this purpose, ultrasonic waves with a frequency of at least 50 kHz, for example, at least 70 kHz, are suitable. The frequency for generating the standing wave, which runs perpendicularly to the emitting surface and to the second surface of the diffusion membrane parallel thereto, and a distance between the emitting surface and the second surface are matched to one another. For example, the distance is 0.1 to 6 cm, for example, 0.5 to 3 cm.

Alternatively, however, a standing wave running in parallel to an emitting surface of the ultrasound emission unit may also be generated, for example, by means of a so-called "transverse resonator." In one embodiment of the last-mentioned embodiment, the ultrasound emission unit is therefore designed to generate in resonance mode a standing ultrasonic wave in the volume, which standing ultrasonic wave runs in parallel to the diffusion membrane. Frequencies of at least 10 kHz are suitable for this purpose, wherein the above considerations relating to frequency dependence or regulation do of course also apply.

The standing ultrasonic wave running in parallel to the diffusion membrane is made possible by means of a suitable design of the ultrasound emission unit, for example a special resonator geometry. For this purpose, the ultrasound emission unit preferably comprises a duct running in parallel to the diffusion membrane, for example, with a rectangular cross-sectional area, and with medium-contacting openings arranged on opposite end sections of the duct.

In a further embodiment of the present disclosure, the ultrasound emission unit can be operated in a mode outside resonance. If necessary, the same ultrasound emission unit can be operated both in the aforementioned resonance mode and in the mode outside resonance. In the context of this application, resonance mode or mode outside resonance always means a resonance within the medium. In the case of the mode outside resonance, this therefore means that no resonant vibrations, such as a standing wave, are present in the medium itself; however, of course, resonance phenomena can nevertheless occur in the sensor itself or in its components, such as the ultrasound emission unit.

In one embodiment of this further development, the ultrasound emission unit is designed to emit ultrasonic waves at intensities and/or frequencies, at which intensities cavitation is present in the volume.

In one embodiment of the further development, the ultrasound emission unit is designed to emit ultrasonic waves with a frequency between 1 MHz and 100 MHz. So-called Eckart flow is generated at such high frequencies. The Eckart flow is described, for example, in the scientific publication by M. Wiklund et al., Lab Chip, 2012, 12, 2438-2451 and the references given therein. The Eckart flow is a directed flow away from the ultrasound emission unit. For this reason, the emitting surface is preferably parallel to the diffusion membrane.

In one embodiment of the present disclosure, the ultrasound emission unit has a piezo element. The piezo element serves, for example, as the ultrasonic transducer of the ultrasound emission unit.

In one embodiment of the present disclosure, the gas sensor is selected from the group of the following: a $CO_2$ gas sensor, an $O_2$ gas sensor, a $CH_4$ gas sensor. Of course, the sensor is not limited to the gas sensors indicated here. The particular way the gas sensor functions in the measurement chamber is immaterial to the present disclosure. For example, the gas sensor is designed as an optical gas sensor in which the concentration of the gaseous analyte in the measurement chamber can be determined by means of spectroscopic analysis methods, for example, non-dispersive infrared spectroscopy (NDIR).

In one embodiment of the present disclosure, the sensor has a response time of less than 5 minutes, for example, less than 2 minutes.

In one embodiment of the present disclosure, the sensor has a response time, which response time is at most half as long as a response time of an otherwise identically designed sensor, without an ultrasound emission unit generating the mixing of the medium in a volume of the medium adjacent to the medium-contacting second surface. By the ultrasound emission unit mixing the medium, the response time is therefore at least halved or is even shorter.

Regarding the method of the present disclosure, the object is achieved by a method for determining a measurand dependent on a concentration of a gaseous analyte in a liquid medium, comprising the steps: introducing ultrasonic waves into the medium, whereby mixing of the medium is generated in a volume adjacent to the medium-contacting second surface; diffusing the gaseous analyte through the diffusion membrane into the measurement chamber; generating a measurement signal dependent on the concentration of gaseous analyte in the measurement chamber; and determining the measurand on the basis of the measurement signal.

BRIEF DESCRIPTION OF THE DRAWINGS

The sensors and methods of the present disclosure are explained in more detail below with reference to exemplary embodiments. The same parts are labeled with the same reference sign in all figures; for reasons of clarity or if it appears sensible for other reasons, reference signs already mentioned are dispensed with in the following figures, which include.

DETAILED DESCRIPTION

Figure 1:
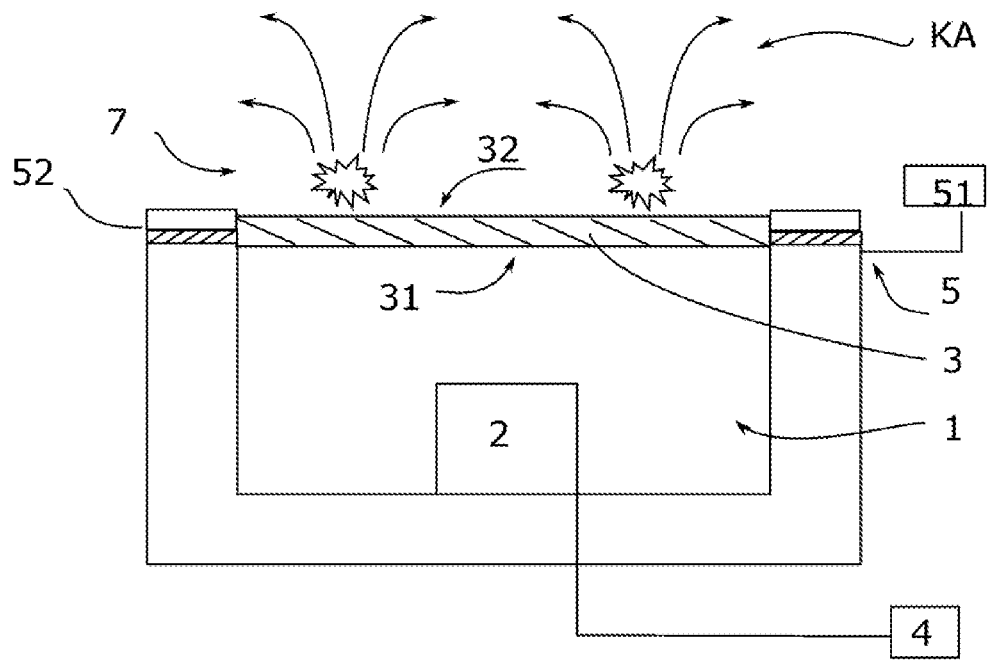
FIG. 1 shows a first embodiment of a sensor according to the present disclosure.

FIG. 1 shows a sectional view of a schematic structure of a first embodiment of a sensor according to the present disclosure for determining the measurand dependent on a concentration of a gaseous analyte in a liquid medium.

The sensor includes a gas sensor 2 which is arranged in a closed measurement chamber 1 and connected to an evaluation unit 4. The measurement chamber 1 is closed off at an upper end by the diffusion membrane 3, which is impermeable to liquid and permeable to a gaseous analyte, wherein the measurement chamber 1 faces a first surface 31 of the diffusion membrane 3. In contrast, the second surface 32 of the diffusion membrane 3 is medium-contacting, i.e., in contact with the medium, when determining the measurand dependent on the concentration of the gaseous analytes in the liquid medium 6 in operation. The gaseous analyte diffuses through the diffusion membrane 3 from the liquid medium into the measurement chamber 1. The liquid medium 6 (not shown in FIG. 1) remains outside the measurement chamber 1. The gas sensor 2 is designed to determine the concentration of gaseous analyte in the gas contained in the measurement chamber 1.

According to the present disclosure, the sensor comprises an ultrasound emission unit 5, which comprises, for example, at least one transducer unit 52 with an ultrasonic transducer for converting an excitation signal into ultrasonic waves and an excitation unit 51 for generating the excitation signal, for example, by means of electronic components configured for this purpose. In the embodiment shown in FIG. 1, the ultrasonic transducer of the transducer unit 52 is designed in its form as a transducer unit comprising or surrounding the membrane at its edge. For example, the transducer unit is annular in the case of a circular membrane or rectangular in the case of a rectangular membrane, etc. The transducer unit 52 comprises a piezo element and/or another transducer element known from the prior art and designed to convert the electronic excitation signal into ultrasonic waves, such as a magnetostrictive transducer.

The embodiment of the sensor shown in FIG. 1 is suitable for the case in which the ultrasound emission unit 5 is operated in a mode outside resonance. Here, cavitation KA is effected in a volume 7 adjacent to the second surface 32 by means of a suitable ultrasound intensity of the ultrasonic waves introduced into the medium 6. Cavitation KA is typically present at ultrasonic frequencies between 10 and 30 kHz and at suitable intensities. In the case of cavitation KA, with sufficient ultrasound intensity, the strong pressure fluctuations of the ultrasonic waves generate gas bubbles which grow and collapse again. As a result of the collapse of the bubbles, turbulent (i.e., non-directed) flows arise which cause the medium 6 to be mixed in the volume 7 adjacent to the second surface 32. The vapor bubbles generated during cavitation KA thus ensure a turbulent flow and thereby a mixing of the liquid medium 6 in the volume 7.

In addition, blocking of the pores of the diffusion membrane 3 can be counteracted at the same time. The ultrasound intensity should be selected such that sufficient mixing and cleaning of the diffusion membrane 3 takes place, but damage to the diffusion membrane 3 by possibly excessive vibrations is avoided. The latter also depends on the respective embodiment of the corresponding diffusion membrane 3, and any further specification therefore does not make sense here.

Figure 2:
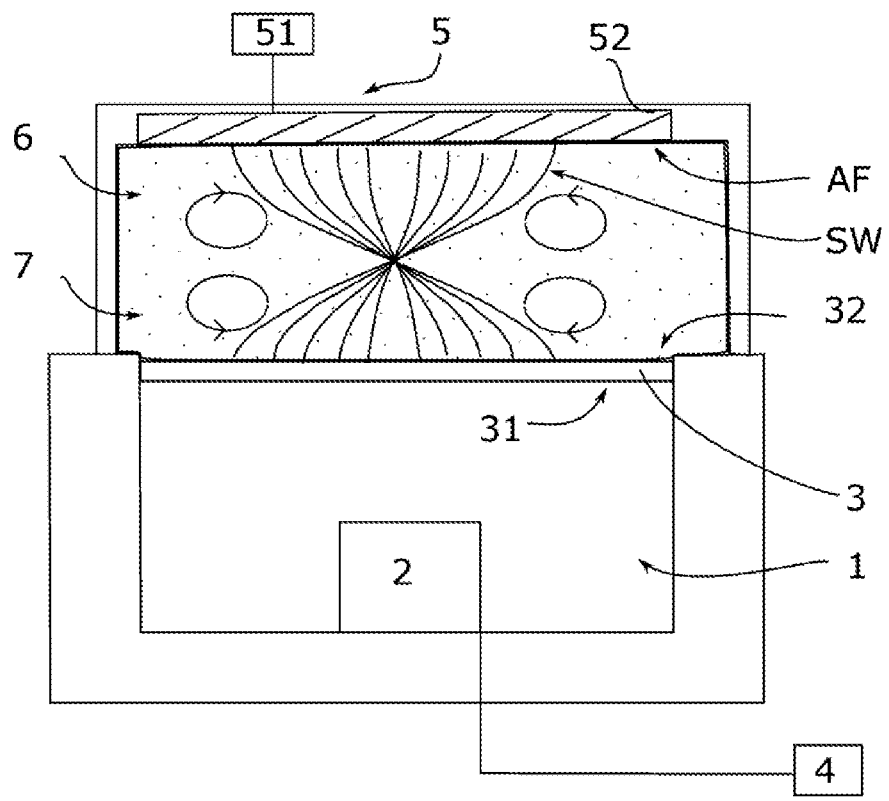
FIG. 2 shows a further embodiment of a sensor according to the present disclosure.

In contrast, FIG. 2 shows a further embodiment of the sensor in which the ultrasound emission unit 5 generates a standing wave between the ultrasound emission unit 5 and the diffusion membrane 3 in resonance mode. In the embodiment shown in FIG. 2, an emitting surface AF of the ultrasound emission unit 5 is arranged substantially in parallel to the diffusion membrane 3. In this embodiment, the medium 6 is provided, for example, in the space formed between the diffusion membrane 3 and the emitting surface AF being open at the sides. Unlike the measurement chamber 1, this space is therefore not a closed chamber in FIG. 2 or in FIG. 1 (nor in the following exemplary embodiments in FIG. 3 and FIG. 4).

The ultrasonic frequency for generating the standing wave SW, which runs perpendicularly to the emitting surface AF and to the second surface 32 of the diffusion membrane 3 that is parallel thereto, is matched to the distance between the emitting surface and the second surface. For example, the distance is a few centimeters, for example, 2 cm, so that a standing wave SW is generated with at least one node between the two surfaces.

The velocity of sound in the liquid medium 6 is dependent on physical and/or chemical state variables of the medium, e.g., temperature and/or pressure, but also on the concentration of the gaseous analyte in the medium 6 itself. For this reason, these state variables also influence the ultrasonic frequency required for generating the standing wave SW, given the resonator geometry.

For this reason, this ultrasonic frequency is, for example, first estimated and adjusted via the expected concentration of gaseous analyte when used as intended over the measurement range of the sensor (for example, from 0.02-20 mmol $CO_2$/l for $CO_2$) and for normal conditions (i.e., normal pressures in the vicinity of atmospheric pressure of about 1013 hPa and normal temperatures in the vicinity of room temperature of about 25° C.). In the case of use in process automation in which the sensor is exposed to typical process conditions, e.g., temperatures of 0-80° C., this estimate for the ultrasonic frequency changes accordingly.

The actual ultrasonic frequency in a specific measurement operation of the sensor under specific state variables is then tracked or adjusted, if necessary, by a regulation. This, for example, by means of the excitation unit 51 and/or the evaluation unit 4, which for this purpose is/are also configured for regulating the excitation signal. If the state variables are detected by other sensors, the measured value thereof can of course also be used for estimating, adjusting and/or regulating the ultrasonic frequency.

The evaluation unit 4 may include one or more computing devices having memory, processing, and/or communication hardware. The evaluation unit 4 may be a single device or a distributed device, and the functions of the evaluation unit 4 may be performed by hardware and/or software. In at least one embodiment, the evaluation unit 4 is programmable to execute algorithms and process data in accordance with operating logic that is defined by programming instructions, such as software or firmware. Alternatively or additionally, operating logic for the evaluation unit 4 can be at least partially defined by hardwired logic or other hardware, for example, using an Application-Specific Integrated Circuit (ASIC) of any suitable type. The evaluation unit 4 can be exclusively dedicated to the functions described herein or may be further used in the regulation, control, and activation of one or more other subsystems or aspects of the sensor.

The flows mixing the medium 6 are generated in the volume 7 by the standing wave SW (see circles with arrows). For the idea according to the present disclosure of mixing and removing the depleted boundary layer, it is not essential here for the standing wave to run perpendicularly to the diffusion membrane 3 in the resonance mode as shown in FIG. 2.

Figure 3:
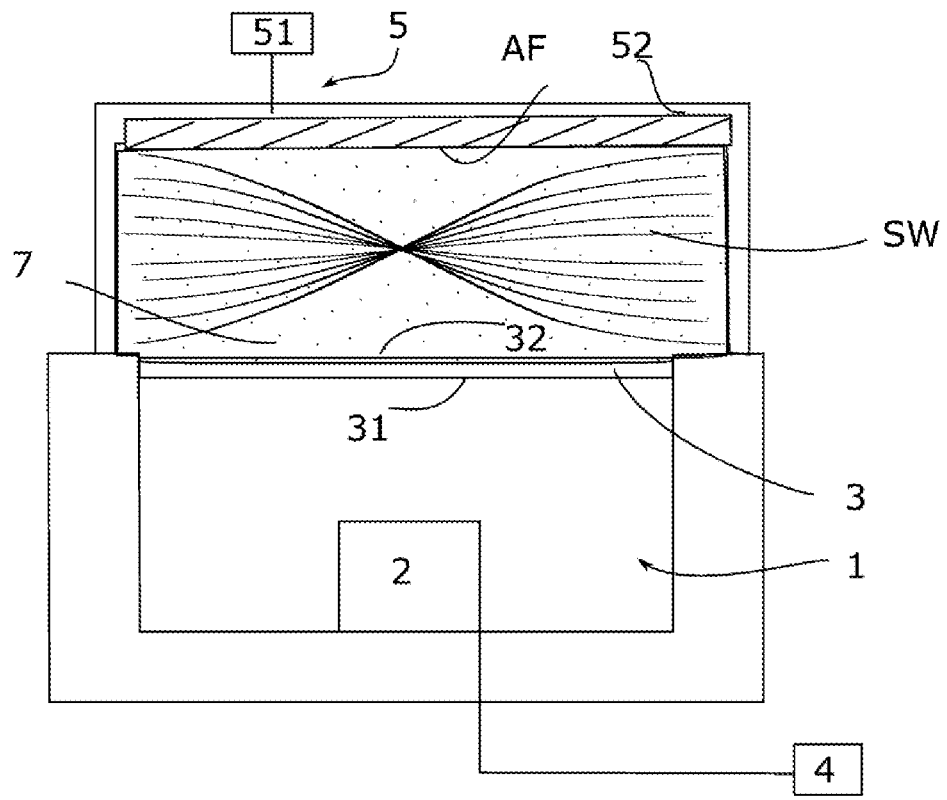
FIG. 3 shows a further embodiment of a sensor according to the present disclosure.

In a further embodiment, shown in FIG. 3, in a resonance mode, a standing wave SW is generated, for example, which runs in parallel to the emitting surface AF and to the diffusion membrane 3—in this context, a so-called transverse resonator. This "transversely running" standing wave SW also ensures a corresponding mixing of the medium 6 in the volume 7 adjacent to the second surface 32. In the case shown here, the emitting surface AF and the diffusion membrane 3 are parallel to one another. However, this does not have to be the case; for example, in another embodiment, the emitting surface AF can also be inclined such that it runs in parallel to the plane of the paper. In this case, the emitting surface AF and the diffusion membrane 3 would therefore be perpendicular to one another.

Figure 4:
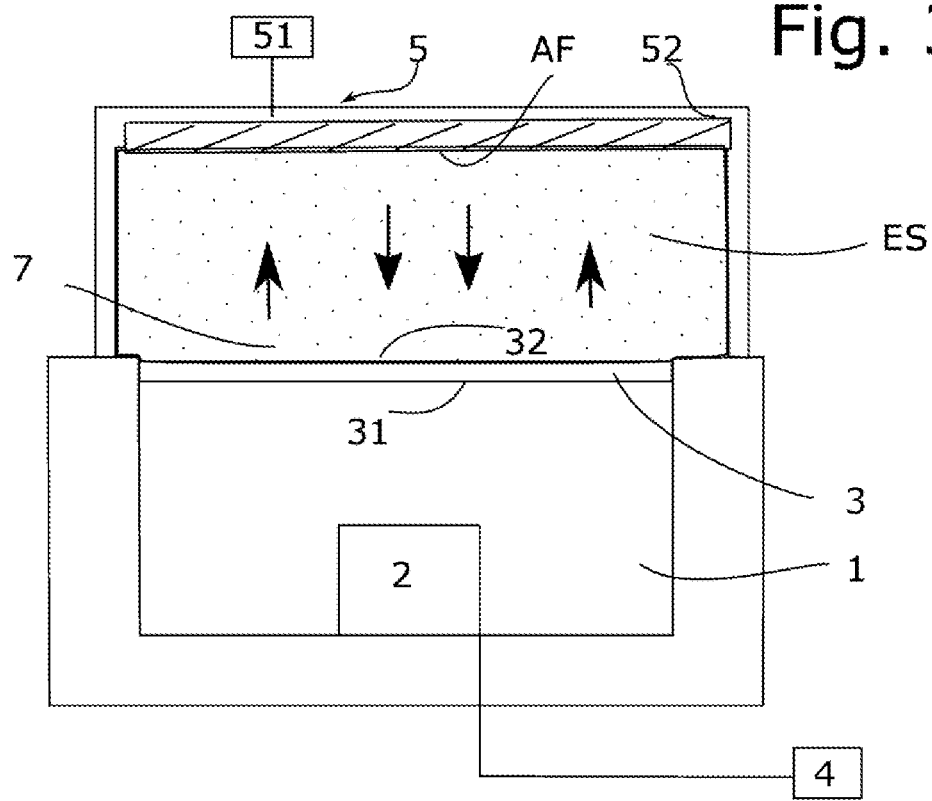
FIG. 4 shows a further embodiment of the sensor according to the present disclosure.

FIG. 4 shows (as in FIG. 1) a further mode outside resonance. In this exemplary embodiment, a so-called Eckart flow ES as already mentioned herein is generated by emitting higher-frequency ultrasonic waves at a frequency between 1 MHz and 100 MHz. The Eckart flow is a directed flow away from the ultrasound emission unit; see the middle arrows. For this reason, the emitting surface AF is preferably parallel to the diffusion membrane 3 here. At the same time, there are still lateral backflows from the diffusion membrane 3 toward the emitting surface AF; see the outer arrows. Even when such an Eckart flow ES is present, the mixing of the medium 6 according to the present disclosure in the volume 7 is therefore realized by ultrasonic waves.

The various operating modes shown in the exemplary embodiments (resonance mode and mode outside resonance) can, of course, also be combined, e.g., in that the same sensor is designed to be operated both in resonance mode and in a mode outside resonance. For example, in FIG. 2 or 3 and 4, the arrangement of the emitting surface AF with respect to the diffusion membrane 3 is substantially unchanged. In order to combine the resonance mode with the mode outside resonance (for example, alternately or even simultaneously), the ultrasound emission unit 5 or its excitation unit 51 and transducer unit 52 can accordingly comprise a plurality of transducer elements and/or excitation elements.

Of course, the present disclosure is not limited to this type of form shown here of the ultrasound emission unit 5 with a straight emitting surface AF. There are no fundamental restrictions on the exact form of the ultrasound emission unit 5. For example, it is possible for the ultrasound emission unit to be probe-shaped, i.e., to be designed as a probe. In this case, the probe would dip into the medium 6 in order to introduce the ultrasonic waves, as in the case of a sonotrode.

Regardless of the respective embodiment, the mixing of the medium 6 results in a significant shortening of the response time of the sensor. Applicant has discovered response time is at least halved by the introduction of the ultrasonic waves in comparison to a comparable sensor without an ultrasound emission unit 5. For example, in the case of a $CO_2$ sensor, a t90 time is expected to be less than 5 minutes, even less than 2 minutes. Comparable $CO_2$ sensors, which do not explicitly effect mixing by other methods (for example, by being operated as flow sensors), have response times of approximately 10 min.

The invention claimed is:

1. A sensor for determining a measurand dependent on a concentration of a gaseous analyte in a liquid medium, the sensor comprising:
   a closed measurement chamber including a gas sensor that is sensitive to the gaseous analyte and configured to generate a measurement signal that is dependent on the concentration of the gaseous analyte in the measurement chamber;
   a diffusion membrane that is impermeable to liquid and gas-permeable to the gaseous analyte, which diffusion membrane closes off a side of the measurement chamber, the diffusion membrane including a first surface facing the measurement chamber and a medium-contacting second surface;
   an evaluation unit configured to determine the measurand based on the measurement signal of the gas sensor; and
   an ultrasound emission unit, which is configured to introduce ultrasonic waves into the medium such that a mixing of the medium is generated in a volume adjacent to the medium-contacting second surface.

2. The sensor of claim 1, wherein the ultrasound emission unit is configured to emit ultrasonic waves at a frequency of at least 20 kHz.

3. The sensor of claim 1, wherein the ultrasound emission unit comprises an emitting surface adapted for emitting the ultrasonic waves and arranged substantially parallel to the diffusion membrane.

4. The sensor of claim 1, wherein the ultrasound emission unit is configured to be operated in a resonance mode as to generate a standing wave in the volume between the ultrasound emission unit and the diffusion membrane.

5. The sensor of claim 4, wherein the ultrasound emission unit is configured to generate a standing ultrasonic wave in the resonance mode, which standing ultrasonic wave extends perpendicular to the emitting surface and the diffusion membrane.

6. The sensor of claim 4, wherein the ultrasound emission unit is configured to generate a standing ultrasonic wave in the resonance mode, which standing ultrasonic wave extends parallel to the diffusion membrane.

7. The sensor of claim 1, wherein the ultrasound emission unit is configured to be operated in a mode outside resonance.

8. The sensor of claim 7, wherein the ultrasound emission unit is configured to emit ultrasonic waves at desired intensities and/or frequencies, at which desired intensities and/or frequencies cavitation occurs in the medium in the volume.

9. The sensor of claim 7, wherein the ultrasound emission unit is configured to emit ultrasonic waves at a frequency between 1 MHz and 100 MHz.

10. The sensor of claim 1, wherein the ultrasound emission unit includes a piezo element.

11. The sensor of claim 1, wherein the gas sensor is one of: a $CO_2$ gas sensor, an $O_2$ gas sensor and a $CH_4$ gas sensor.

12. The sensor of claim 1, wherein the sensor is configured to provide a response time of less than 5 minutes.

13. The sensor of claim 1, wherein the sensor is configured to provide a response time, which response time is at most half as long as a conventional response time of a different sensor, which does not include an ultrasound emission unit, which generates mixing of the medium adjacent to a medium-contacting surface of the different sensor.

14. A method for determining a measurand dependent on a concentration of a gaseous analyte in a liquid medium, the method comprising:
   providing the sensor according to claim 1;
   introducing ultrasonic waves into the medium such that mixing of the medium is generated in the volume adjacent to the medium-contacting second surface;
   diffusing the gaseous analyte through the diffusion membrane into the measurement chamber;
   generating a measurement signal from the gas sensor, which measurement signal is dependent on the concentration of the gaseous analyte in the measurement chamber; and
   determining the measurand based on the measurement signal.

* * * * *